United States Patent
Ikushima et al.

(10) Patent No.: US 7,144,253 B2
(45) Date of Patent: Dec. 5, 2006

(54) DENTAL DIAMOND BUR

(75) Inventors: Keisuke Ikushima, Tokyo (JP); Koichi Mamada, Tokyo (JP)

(73) Assignee: GC Corporation, Tokyo (JP)

( * ) Notice: Subject to any disclaimer, the term of this patent is extended or adjusted under 35 U.S.C. 154(b) by 473 days.

(21) Appl. No.: 10/671,744

(22) Filed: Sep. 29, 2003

(65) Prior Publication Data
US 2004/0063068 A1 Apr. 1, 2004

(30) Foreign Application Priority Data
Sep. 30, 2002 (JP) ............... 2002-285999

(51) Int. Cl.
*A61C 3/06* (2006.01)
(52) U.S. Cl. ................................. 433/166
(58) Field of Classification Search .......... 433/165, 433/166; 51/295, 309
See application file for complete search history.

(56) References Cited

U.S. PATENT DOCUMENTS

| | | | | |
|---|---|---|---|---|
| 3,309,772 A | * | 3/1967 | Lieb et al. | 433/166 |
| 4,897,037 A | * | 1/1990 | Appleby | 433/166 |
| 6,106,369 A | * | 8/2000 | Konishi et al. | 451/41 |
| 6,267,595 B1 | * | 7/2001 | Gratz | 433/165 |
| 6,565,356 B1 | | 5/2003 | Oyamada et al. | |
| 6,602,111 B1 | * | 8/2003 | Fujie et al. | 451/36 |
| 2004/0018468 A1 | * | 1/2004 | Gorokhovsky | 433/166 |

* cited by examiner

*Primary Examiner*—Todd E. Manahan
(74) *Attorney, Agent, or Firm*—Oblon, Spivak, McClelland, Maier & Neustadt, P.C.

(57) ABSTRACT

A dental diamond bur having grains of diamond attached to a head of the bur body with a plated metal layer containing grains of a fluorine compound that are almost uniformly dispersed and have an average diameter smaller than that of the diamond.

3 Claims, 1 Drawing Sheet

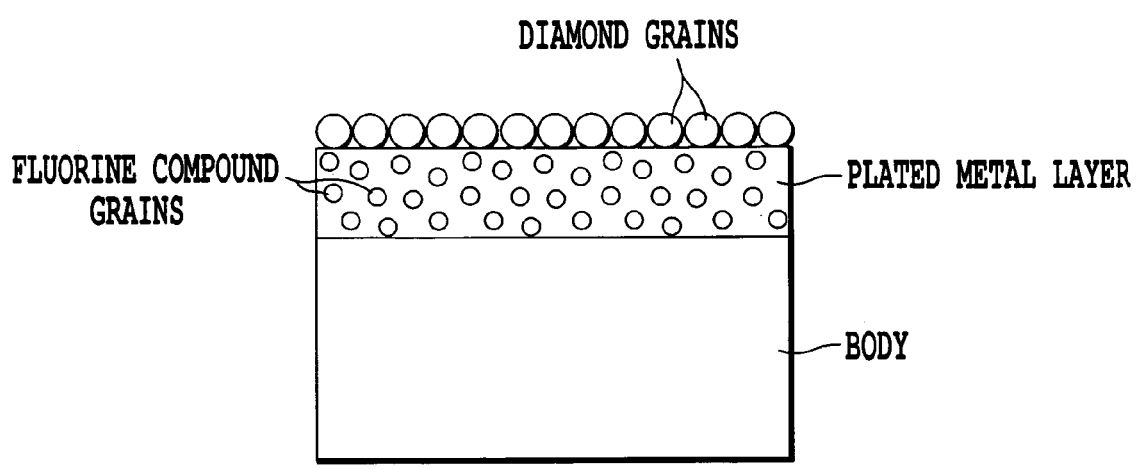

DENTAL DIAMOND BUR

BACKGROUND OF THE INVENTION

1. Field of the Invention

The present invention is for a dental diamond bur used in a clinical dental treatment and in a dental laboratory for cutting and shaving natural teeth and dental prosthesis such as dental filling materials, dentures and artificial teeth.

2. Description of the Conventional Art

The conventional dental diamond burs used in clinical dental treatments and in dental laboratories have been the type with either natural or artificial diamonds electro-deposited onto a plated metal layer such as a plated nickel layer at the head of a stainless bar that has been shaped into a desired form for cutting and shaving purposes (See, for example, Japanese Patent Publications No. 63-234963 and No. 11-113926). The dental diamond burs having diamond grains, the material known as the hardest, for cutting and shaving, are not only used for teeth, but also widely used dental materials such as resins, metals and ceramics.

However, when this type of dental diamond bur is used in a dental laboratory for cutting and shaving dental prostheses such as dentures and artificial teeth made from resins, rising temperature at the cutting surface causes cutting debris to lodge and clog between diamond grains. With the cutting grains of diamond no longer exposed, the cutting efficiency is thus deteriorated extremely and the excess cutting time is required. It is also a laborious task in cleaning the entangled debris.

Furthermore, it is difficult to wash away the cutting debris during grinding and shaving natural teeth or dental prostheses in the mouth cavity even with water spraying. This results in more time required and more pains to patients as the cutting efficiency diminishes.

The task for the present invention is to provide a dental diamond bur that is free of the shortcomings present in the use of a conventional dental diamond bur as mentioned above by making it more difficult for cutting debris to entangle on the bur and also by making the bur superior in debris removal easiness and cutting feelings.

SUMMARY OF THE INVENTION

With the task of eliminating the aforementioned shortcomings in mind, the inventors devoted themselves in extensive research efforts for solving the problems and thought that the cutting efficiency of the dental diamond bur should increase when the cutting surface to which the diamond grains were attached, was made water repellent. For the water repellent properties, attentions were turned to study the structure of the leaf of a water lily, a typical water repellent plant found in nature. The leaf has a complicated surface formation consisting of a fractal structure and the surface of the leaf is covered with aquaphobic materials. It is the combination of this fractal structure and the aquaphobic materials that makes it highly water repellent. In general, fluorine compounds have lower surface energy. For example, $SiO_2$ has surface energy of 200 dyne/cm while tetrafluoroethylene polymer has only 18.5 dyne/cm. On the other hand, the attractive forces of water arise from the van der Waals force and hydrogen bonding force. Therefore, in a highly aquaphilic substance, these forces give stronger bonding, for which the required energy is 73 dyne/cm. Consequently, if the energy is less than this required value, it can be made aquaphobic. The inventors then zeroed in on the fractal structure of the head of the bur body to which the diamond grains are attached, and by adding there low surface energy grains of a fluorine compound, an extremely effective water repellent dental diamond bur was invented.

BRIEF DESCRIPTION OF THE DRAWINGS

The FIGURE shows an embodiment of the dental diamond bur of the present invention.

DESCRIPTION OF THE PREFERRED EMBODIMENTS

The present invention is for a dental diamond bur wherein grains of diamond having an average diameter of 0.01 to 50 μm are attached to the head of the bur body with a plated metal layer containing grains of a fluorine compound that are almost uniformly dispersed and have an average diameter smaller than that of the diamond. The desirable volume fraction of the grains of the fluorine compound in the plated metal layer is 0.1 to 60%.

As described above, when the plated metal layer located at the head of the bur body to which the diamond grains are attached, also contains almost uniformly the fluorine compound grains with the specified average diameter range smaller than that of the diamond grains, the cutting feelings of the bur will improve. This is because the tip is water repellent due to the lowered surface energy toward water and the cutting diamond grains remain exposed, resulting in that it is harder for the cutting debris to get entangled and clogged on the surface and their removal will be undemanding.

Furthermore, when the plated metal layer is a plated nickel layer, the hardness of the plated metal layer, which is decreased by the addition of a fluorine compound, will increase upon addition of 0.1 to 15% by weight of a phosphorus compound due to the complex formation between nickel and phosphorus.

Some examples of the fluorine compounds that could be used in the present invention are listed below. So long as they are these commonly known materials, there are no specific requirements as to which compound should be used, or what are the raw materials or processes that are followed in manufacturing them: tetrafluoro-ethylene polymer, 4-fluoroethylene polymer, perfluoroalkoxy polymer, 6-fluoropropylene/ethylene copolymer, 4-fluoroethylene/ethylene co-polymer, perfluoromethylvinylether polymer, perfluoroalkylethyl-(meta)acrylate polymer, perfluorosulfonide polymer, fluoroacetylene polymer, fluoromaleic acid polymer, fluorographite, chlorotrifluoroethylene polymer, and 1,4-cyclohexylenedimethylene terephthalate polymer.

The average grain diameter of these fluorine compounds must be smaller than that of the diamonds attached to the head of the bur body, and must be in the range of 0.01 to 50 μm. If the average grain diameter of the fluorine compound were larger than that of the attached diamond grains, they will be present at the cutting surface instead of the diamond grains, and good cutting efficiency cannot be achieved. The thickness of the plated metal layer on a dental diamond bur will depend on the shape of the bur and the kind of metal used, and is generally in the range of 100 to 150 μm. The average grain diameter should range 0.01 to 50 μm in order to be almost uniformly present in the plated metal layer, and preferably 0.1 to 5 μm. If the average grain diameter of the fluorine compound is less than 0.01 μm, then the grains tend to cohere, while if the average diameter is greater than 50 μm, the grains are liable to detach from the plated surface due to friction.

In general, the plated metal layer at the head of the bur body to which the diamond grains are attached, can be formed either by non-electrolytic or electrolytic plating method. In formation of the plated metal layer, when the metal layer is formed from co-deposition of metal and the grains of a fluorine compound as in the present invention, poor adhesion of the plated metal layer to the substrate will result as the volume fraction of the co-deposition is increased. Considering the adhesion of the plated metal layer to the front tip of the bur body, it is desirable to limit the volume fraction of the fluorine compound grains to less than 60%. On the other hand, when the volume fraction of fluorine compound grains is too low, the water repellency will be compromised, and, therefore, the volume fraction is held at 0.1 to 60% and preferably at 3 to 50%.

When the plated metal layer is a plated nickel layer widely used for a plated metal layer of the dental diamond bur, addition of 0.1 to 15% by weight of a phosphorus compound will, by complex formation between nickel and phosphorus, result in enhancement of the hardness of the plated metal layer which is reduced by the addition of the fluorine compound. The phosphorous compounds are nonspecific and can be any of the following for example: phosphorous acid, ethyl phosphite, diethyl phosphite, dibutyl phosphite, triethyl phosphite, tri-butyl phosphite, trimethyl phopshite, disodium phosphite penta-hydrate, hypophosphorous acid, and sodium hypophosphite.

As stated above, the plated metal layer at the front tip of the bur body to which the diamond grains are attached, is formed either by a non-electrolytic or electrolytic plating method, and the phosphorus compound is added to a nickel-plating solution. If insufficient amount is added, the hardness of the plated metal layer is hard to improve, and, on the other hand, if an excessive amount were added, the plating condition would be hard to be optimized due to its low pH values. A desirable range is thus 0.1 to 15% by weight and, preferably, 0.1 to 10% by weight. Furthermore, after the formation of the plated metal layer, it is possible to further enhance its surface hardness by a heat treatment at 70 to 300° C.

For a plating solution to form the plated metal layer at the head of a dental diamond bur to which the grains of diamond are attached, by either non-electrolytic or electrolytic plating method, use can be made of aqueous solution of a base of the metal that is to form the matrix of the plated metal layer. A plating solution, for example, containing nickel, chromium and their alloys can be used. The compositions of these solutions are known to the public and are published in Japanese Patent Publications No. 4-285199, No. 6-306626, No. 7-90691, and No. 2000-17491. Following these compositions, the grains of a fluorine compound that are dispersed in the aqueous solution of the metal base, can be attached onto the head of bur body with the metals that form a matrix.

In the plating solution from which the plated metal layer is to form on the dental diamond bur of the present invention, it is necessary to use a surface active agent for uniformly dispersing the highly water repelling fluorine compound in the plating solution. They can be, for example, water-soluble cationic series, nonionic series, and an ampholytic surface active agent series that show cationic characters at the pH of the plating solution. It is especially desirable to have fluorine series surface active agents having C—F bonds in the molecules, because the aquaphobic groups are strongly adsorbed to the surface of the fluorine compound while the aquaphilic groups are arranged on the outside of the grains.

For plating conditions of forming the plated metal layer on the dental diamond bur of the present invention, suitable choices can be made according to the types of plating solutions, and the common practice in temperature settings for the solutions, pH values and current values can be adopted. Also, the stirring method for the plating solution during the electro-deposition is nonspecific, and the usual mechanical stirring such as a screw stirring or a magnetic stirring can be adopted.

The following is only illustrative examples of the present invention, and is not to be construed as the limitation of the present invention.

Test pieces were prepared as follows.

For measuring the contact angle and the hardness of the plated metal layer, piecse of stainless steel plates, 10 mm in width, 10 mm in length and 0.1 mm in thickness, were plated without diamond grains. For evaluating the cutting time, removal of cutting debris and cutting characteristics, stainless steel rods with its shapes conforming to ISO 203/018 were plated to attach diamond grains for making dental diamond burs.

Adjustments for plating solutions and the conditions for plating were as follows.

A plating solution was made by mixing one liter of distilled water with 420 grams of nickel sulfamate, 45 grams of nickel chloride and 40 grams of boric acid and the resulting mixture had a pH value of 3.9. After 20 minutes of electroplating at a current of 15 mA, the average thickness of the plated metal layer was 150 μm.

The following methods were used in evaluation.

(1) Contact Angle

Face contact angle meter (trade name: CONTACT-ANGLEMETER, made by Kyowa Interface Science Co., Ltd.) was used to measure the contact angles between water and the plated metal layers without attachment of diamond grains by following the liquid drop method. The results are summarized in Table 1.

(2) Surface Hardness

By conforming to JIS Z2244 "Vickers Hardness Testing Methods", the Vickers hardness (Hv) of the plated metal layers without diamond grains was measured and the results are summarized in Table 1.

(3) Cutting Time

Dental diamond burs with diamond grains attached to their plated metal layer were used in cutting 5 mm thick composite blocks (Trade name: GN-I Composite Block, made by GC Corporation) parallelly to the composite blocks with a feather touch at a speed of 300,000 rpm. The times needed for perforating 5 mm thickness were measured and the results are summarized in Table 1.

(4) Removal of Cutting Debris

Dental diamond burs with diamond grains attached to their plated metal layers were used in cutting composite blocks (Trade name: GN-I Composite Block, made by GC Corporation) at a speed of 300,000 rpm. Evaluations were conducted for the removal of the cutting debris in two categories: removal with ease and removal with difficulty. The results are summarized in Table 1

(5) Cutting Characteristics

Dental diamond burs with diamond grains attached to their plated metal layers were used in evaluating the cutting feelings by cutting soft dentin at a speed of 300,000 rpm, and the Table 1 summarizes their ratings in two categories: good or poor.

EXAMPLE 1

Grains of tetrafluoroethylene polymer (Trade name: Lubron, made by Daikin Industries, Ltd., average grain diameter 0.5 µm) were added at 45 g/L, to nickel sulfamate electrolysis bath with the aforementioned composition. Also, a surface active agent (Trade name: Unidyne, made by Daikin Industries, Ltd.) was added according to a ratio of 40 mg of the agent to one gram of tetrafluoroethylene polymer grains. In the case where diamond grains were to be attached to the plated metal layer for a dental diamond bur, a nickel sulfamate solution with the aforementioned composition and containing 2 Kg of diamond grains with an average diameter of 100 µm was used.

EXAMPLE 2

Grains of fluorographite (Trade name: Cefbon, made by Central Glass Co., Ltd., average grain diameter 2 µm) were added at 45 g/L, to nickel sulfamate electrolysis bath with the aforementioned composition. Also, a surface active agent (Trade name: Unidyne, made by Daikin Industries, Ltd.) was added according to a ratio of 40 mg of the agent to one gram of fluorographite grains. In the case where diamond grains were to be attached to the plated metal layer for a dental diamond bur, a nickel sulfamate electrolysis bath with aforementioned composition and containing 2 Kg of diamond grains with an average diameter of 100 µm was used.

EXAMPLE 3

Grains of tetrafluoroethylene polymer (Trade name: Lubron, made by Daikin Industries, Ltd., average grain diameter 0.5 µm) at 45 g/L, and phosphorous acid at 2 g/L were added to nickel sulfamate electrolysis bath with the aforementioned composition. Also, a surface active agent (Trade name: Unidyne, made by Daikin Industries, Ltd.) was added according to a ratio of 40 mg of the agent to one gram of tetrafluoroethylene polymer grains. In the case where diamond grains were to be attached to the plated metal layer for a dental diamond bur, a nickel sulfamate electrolysis bath with the aforementioned composition and containing 2 Kg of diamond grains with an average diameter of 100 µm was used.

COMPARATIVE EXAMPLE 1

A nickel sulfamate electrolysis bath with the aforementioned composition was used. In the case where diamond grains were to be attached to the plated metal layer for a dental diamond bur, a nickel sulfamate electrolysis bath with the aforementioned composition and containing 2 Kg of diamond grains with an average diameter of 100 µm was used.

TABLE 1

| | | Example 1 | Example 2 | Example 3 | Comparative Example 1 |
|---|---|---|---|---|---|
| Fluoro-compound grains | | Tetra-Fluoro-ethylene polymer | Fluoro-graphite | Tetra-Fluoro-ethylene polymer | — |
| Phosphorus compound | | — | — | Phosphorus Acid | — |
| Plated metal layer | Contact Angle | 108° | 125° | 120° | 60° |
| | Surface Hardness | 480 | 480 | 600 | 500 |
| Dental Diamond Bur | Cutting time | 30 sec | 29 sec | 32 sec | 55 sec |
| | Removability of debris | easy | easy | easy | Difficult |
| | Cutting feelings | Good | Good | Good | Poor |

As is clear from Table 1, a dental diamond bur according to the present invention makes the cutting debris difficult to entangle on the bur, and thus greatly reduces the cutting time when compared to the Comparative Example 1, and it is also superior in debris removal and the cutting feelings. Also, when the plated metal layer is nickel, the presence of 0.1 to 15% by weight of phosphorus compound, as is the case in the Example 3, increases not only the contact angle of the plated metal layer, but also the surface hardness, and the cutting diamond grains are more firmly attached. Thus, the present invention contributes greatly to the field of the dental care.

What is claimed is:

1. A dental diamond bur wherein grains of diamond having an average diameter of 0.01 to 50 µm are attached to a head of the bur body with a plated metal layer containing grains of a fluorine compound that are almost uniformly dispersed and have an average diameter smaller than that of the diamond.

2. A dental diamond bur as claimed in claim 1, wherein the volume fraction of the grains of the fluorine compound in the plated metal layer is 0.1 to 60%.

3. A dental diamond bur as claimed in claim 1 or 2, wherein the plated metal layer is a plated nickel layer and the layer further contains 0.1 to 15% by weight of a phosphorus compound.

* * * * *